US011154577B2

(12) United States Patent
Petrucci

(10) Patent No.: US 11,154,577 B2
(45) Date of Patent: *Oct. 26, 2021

(54) AMNION COATED EMBOLIC AGENTS FOR TREATING TUMORS

(71) Applicant: Gary M. Petrucci, Long Lake, MN (US)

(72) Inventor: Gary M. Petrucci, Long Lake, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/378,001

(22) Filed: Apr. 8, 2019

(65) Prior Publication Data
US 2019/0298776 A1 Oct. 3, 2019

Related U.S. Application Data

(62) Division of application No. 15/708,413, filed on Sep. 19, 2017, now Pat. No. 10,251,917.

(51) Int. Cl.
A61K 35/50 (2015.01)
A61K 51/10 (2006.01)
A61L 24/00 (2006.01)
A61K 45/06 (2006.01)
A61K 45/00 (2006.01)

(52) U.S. Cl.
CPC .............. A61K 35/50 (2013.01); A61K 45/06 (2013.01); A61K 51/1045 (2013.01); A61L 24/0005 (2013.01); A61L 24/0015 (2013.01); A61K 45/05 (2013.01); A61K 51/1096 (2013.01); A61L 2300/416 (2013.01); A61L 2430/36 (2013.01)

(58) Field of Classification Search
None
See application file for complete search history.

(56) References Cited

U.S. PATENT DOCUMENTS

| 4,828,844 | A | 5/1989 | Rontgen-Odenthal et al. |
| 5,049,389 | A | 9/1991 | Radhakrishnan |
| 5,131,907 | A | 7/1992 | Williams |
| 5,612,028 | A | 3/1997 | Sackier et al. |
| 5,656,498 | A | 8/1997 | Iijima et al. |
| 7,524,489 | B2 | 4/2009 | Messina et al. |
| 7,682,803 | B2 | 3/2010 | Paludan |
| 8,323,701 | B2 | 12/2012 | Daniel et al. |
| 8,357,403 | B2 | 1/2013 | Daniel et al. |
| 8,372,437 | B2 | 2/2013 | Daniel |
| 8,372,438 | B2 | 2/2013 | Daniel et al. |
| 8,372,439 | B2 | 2/2013 | Daniel et al. |
| 8,409,626 | B2 | 4/2013 | Daniel et al. |
| 8,460,715 | B2 | 6/2013 | Daniel |
| 8,460,716 | B2 | 6/2013 | Daniel |
| 8,623,421 | B2 | 1/2014 | Daniel |
| 8,642,092 | B2 | 2/2014 | Daniel et al. |
| 8,703,206 | B2 | 4/2014 | Daniel et al. |
| 8,703,207 | B2 | 4/2014 | Daniel et al. |
| 8,709,493 | B2 | 4/2014 | Daniel et al. |
| 8,709,494 | B2 | 4/2014 | Daniel |
| 8,904,664 | B2 | 12/2014 | Pringle et al. |
| 8,932,643 | B2 | 1/2015 | Daniel et al. |
| 9,039,783 | B2 | 5/2015 | Petter-Puchner |
| 9,080,184 | B2 | 7/2015 | Kharazi et al. |
| 9,084,767 | B2 | 7/2015 | Daniel et al. |
| 9,180,145 | B2 | 11/2015 | Brown et al. |
| 9,186,382 | B2 | 11/2015 | Daniel et al. |
| 9,205,177 | B2 | 12/2015 | Schorgl et al. |
| 9,265,800 | B2 | 2/2016 | Daniel |
| 9,265,801 | B2 | 2/2016 | Daniel |
| 9,272,003 | B2 | 3/2016 | Daniel et al. |
| 9,272,005 | B2 | 3/2016 | Daniel |
| 9,415,074 | B2 | 8/2016 | Daniel et al. |
| 9,433,647 | B2 | 9/2016 | Daniel |
| 9,463,206 | B2 | 10/2016 | Koob et al. |
| 9,533,011 | B2 | 1/2017 | Daniel et al. |
| 9,555,062 | B2 | 1/2017 | Pringle et al. |
| 9,572,839 | B2 | 2/2017 | Daniel |
| 9,655,948 | B1 | 5/2017 | Koob et al. |
| 9,662,355 | B2 | 5/2017 | Koob et al. |
| 9,687,588 | B2 | 6/2017 | Daniel et al. |
| 9,789,137 | B2 | 10/2017 | Daniel et al. |
| 9,827,293 | B2 | 11/2017 | Koob et al. |
| 10,251,917 | B1 | 4/2019 | Petrucci |
| 2003/0187515 | A1 | 10/2003 | Hariri |
| 2003/0229394 | A1 | 12/2003 | Ogle et al. |
| 2003/0235563 | A1 | 12/2003 | Strom et al. |
| 2003/0235580 | A1 | 12/2003 | Zhang |
| 2005/0020500 | A1 | 1/2005 | Shen et al. |
| 2005/0287223 | A1 | 12/2005 | Peyman |
| 2007/0031471 | A1 | 2/2007 | Peyman |
| 2007/0293872 | A1 | 12/2007 | Peyman |
| 2008/0181950 | A1 | 7/2008 | Bates |
| 2009/0238801 | A1 | 9/2009 | Woodbury et al. |
| 2009/0270978 | A1 | 10/2009 | Virkler |
| 2010/0124569 | A1 | 5/2010 | Abbot et al. |
| 2010/0143312 | A1 | 6/2010 | Hariri |
| 2010/0228335 | A1 | 9/2010 | Schorgl |
| 2010/0260721 | A1 | 10/2010 | McGonagie |

(Continued)

FOREIGN PATENT DOCUMENTS

| WO | WO 1998/008492 | 5/1998 |
| WO | WO 2007/038686 | 4/2007 |
| WO | WO 2012/112410 | 8/2011 |
| WO | WO 2012/088396 | 6/2012 |
| WO | WO 2014/047067 | 3/2014 |
| WO | WO 2015/134936 | 9/2015 |
| WO | WO 2016/007554 | 1/2016 |

OTHER PUBLICATIONS

"Angioplasty or bypass surgery?," Harvard Heart Letter, Apr. 2008, 2 pages.

(Continued)

Primary Examiner — Nghi V Nguyen
(74) Attorney, Agent, or Firm — Merchant & Gould P.C.

(57) ABSTRACT

This document provides methods and materials for treating a mammal (e.g., a human) having one or more tumors. For example, embolic agents including an amnion tissue preparation (e.g., amnion coated embolic agents) that can be used in arterial embolization to reduce or eliminate blood flow in a blood vessel that supplies a tumor are provided.

15 Claims, No Drawings

(56) References Cited

U.S. PATENT DOCUMENTS

| | | |
|---|---|---|
| 2011/0307003 A1 | 12/2011 | Chambers |
| 2012/0080030 A1 | 4/2012 | Wachter |
| 2012/0171171 A1 | 7/2012 | West et al. |
| 2012/0201787 A1 | 8/2012 | Abbot et al. |
| 2012/0269785 A1 | 10/2012 | Woods et al. |
| 2013/0071358 A1 | 3/2013 | Peterson |
| 2013/0238100 A1 | 9/2013 | Young |
| 2013/0243739 A1 | 9/2013 | Burt |
| 2014/0271776 A1 | 9/2014 | Vines |
| 2015/0037436 A1 | 2/2015 | Huang et al. |
| 2015/0216910 A1 | 8/2015 | Horton et al. |
| 2015/0216912 A1 | 8/2015 | Koob |
| 2015/0231183 A1 | 8/2015 | Peterson et al. |
| 2015/0335686 A1 | 11/2015 | Spencer et al. |
| 2016/0184479 A1 | 6/2016 | Fette |
| 2016/0193253 A1 | 7/2016 | Petrucci |
| 2016/0193254 A1 | 7/2016 | Petrucci |
| 2016/0199417 A1 | 7/2016 | Werber |
| 2016/0199537 A1 | 7/2016 | Koob |
| 2016/0376305 A1* | 12/2016 | Tseng ............... A61K 47/6957 530/395 |
| 2017/0042943 A1 | 2/2017 | Namin et al. |
| 2018/0338998 A1 | 11/2018 | Petrucci |
| 2018/0369455 A1 | 12/2018 | Petrucci |
| 2019/0083546 A1 | 3/2019 | Petrucci |
| 2019/0083547 A1 | 3/2019 | Petrucci |
| 2019/0083548 A1* | 3/2019 | Morse ............... A61L 27/3604 |

OTHER PUBLICATIONS

Alkilani et al., "Transdermal Drug Delivery: Innovative Pharmaceutical Developments Based on Disruption of the Barrier Properties of the stratum corneum," Pharmaceutics, 2015, 7: 438-470.

Anand et al., "Use of amniotic membrane graft in glaucoma shunt surgery," Opthalmic Surg Lasers Imaging, May-Jun. 2011, 42: 184-9.

Brown et al., "Dermal and Transdermal Drug Delivery Systems: Current and Future Prospects," Drug Delivery, 2006, 13: 175-187.

Chen et al., "Percutaneous Thrombin Injection for Treatment of a Splenic Artery Aneurysm," Radiology case reports, 1(1):13-16, Jan. 2006.

Chen et al., "The effects of acellular amniotic membrane matrix on osteogenic differentiation and ERK1/2 signaling in human dental apical papilla cells," Biomaterials, 2012, 33(2): 455-63.

Derdeyn et al., "Collagen-Coated Acrylic Microspheres for Embolotherapy: In Vivo and In Vitro Characteristics," AJNR Am J Neuroradiol, Apr. 1997, 18:647-653.

Dhote et al., "Iontophoresis: A Potential Emergence of a Transdermal Drug Delivery System," Sci Pahrm, 2012, 80: 1-28.

Diaz-Prado et al., "Human amniotic membrane as an alternative source of stem cells for regenerative medicine," Differentiation, 2011, 81(3): 162-71.

Gerth et al., "Clinical outcomes for Conduits and Scaffolds in peripheral nerve repair," Worls J Clin Cases, Feb. 2015, 3: 141-147.

Hassan et al., "Neural-Differentiated Mesenchymal Stem Cells Incorporated into Muscle Stuffed Vein Scaffold Forms a Stable Living Nerve Conduit," Journal of Orthopaedic Research, Oct. 2012, 1674-1681.

International Preliminary Report on Patentability in Application No. PCT/US2015/068127, dated Jul. 11, 2017, 12 pages.

International Preliminary Report on Patentability in Application No. PCT/US2015/068136, dated Jul. 11, 2017, 11 pages.

International Search Report & Written Opinion in International Application No. PCT/US2018/051651 dated Dec. 6, 2018, 20 pages.

International Search report and Written Opinion in International Application No. PCT/2017/016225, dated Apr. 14, 2017, 18 pages.

International Search report and Written Opinion in International Application No. PCT/US 18/38815, dated Sep. 19, 2018, 16 pages.

International Search Report and Written Opinion in International Application No. PCT/US2015/68127, dated Apr. 19, 2016, 18 pages.

International Search Report and Written Opinion in International Application No. PCT/US2015/68136, dated Feb. 26, 2016, 13 pages.

Interntional Preliminary Report on Patentability in International Application No. PCT/US2017/016225, dated Aug. 16, 2018.

Kalluri and Banga, "Transdermal Delivery of Proteins," AAPS PharmSciTech, Mar. 2011, 12: 431-441.

Khan et al., "Iontophoretic drug delivery: History and applications," Journal of Applied Pharmaceutical Science, 2011, 11-24.

Kumar and Philip, "Modified Transdermal Technologies: Breaking the Barriers of Drug Permeation via the Skin," Tropical Journal of Pharmaceutical research, Mar. 2007, 6: 633-644.

Lei et al., "Dehydrated Human Amnion/Chorion Membrane (dHACM) Allografts as a Therapy for Orthopedic Tissue Repair," Techniques in Orthopaedics, 2017, 9 pages.

Liu, "[Shunt tube implantation combining amniotic membrane transplantation and implantation of Molteno implant for glaucoma after penetrating keratoplasty]," Yan Ke Xue Bao, Jun. 2000, 16: 65-72, abstract only.

McDonald et al., "Maintenance of human amnion epithelial cell phenotype in pulmonary surfactant," Stem Cell Research & Therapy, 2014, 5: 107.

Orth et al., "Current perspectives in stem cell research for knee cartilage repair," Stem Cells Cloning, Jan. 2014, 7: 1-17.

Quint et al., "Decellularized tissue-engineered blood vessel as an arterial conduit," PNAS, May 2011, 108: 9214-9219.

Sabongi et al., "Peripheral nerve regeneration with conduits: use of vein tubes," Neural regen Res, Apr. 2015, 10: 529-533.

Vaidya et al., "An Overview of Embolic Agents," Seminars in Interventional Radiology, 2008, 25: 204-215.

Wilshaw et al., "Production of an acellular amniotic membrane matrix for use in tissue engineering," Tissue Eng., 2006, 12(8): 2117-29.

Zhan et al., "Nanofiber scaffolds facilitate functional regeneration of peripheral nerve injury," Nanomedicine, 2013, 9: 305-315.

Saralidze et al., "New acrylic microspheres for arterial embolization: combining radiopacity for precise localization with immobilized thrombin to trigger local blood coagulation," Biomaterials. May 1, 2007;28(15):2457-2464.

European Search Report for Application No. 18859483.2, dated May 7, 2021, 12 pages.

* cited by examiner

AMNION COATED EMBOLIC AGENTS FOR TREATING TUMORS

CLAIM OF PRIORITY

This application is a divisional of and claims priority to U.S. patent application Ser. No. 15/708,413, filed on Sep. 19, 2017, now U.S. Pat. No. 10,251,917, the entire contents of which are hereby incorporated by reference.

BACKGROUND

1. Technical Field

This document relates to methods and materials for treating a mammal (e.g., a human) having one or more tumors. For example, embolic agents including an amnion tissue preparation (e.g., amnion coated embolic agents) provided herein can be used in arterial embolization to reduce and/or eliminate blood flow in a blood vessel that supplies a tumor.

2. Background Information

Cancer is among the leading causes of death in the United States and worldwide. In 2016, an estimated 1,685,210 new cases of cancer were diagnosed and 595,690 people died from the disease in the US alone (National Cancer Institute Cancer Statistics).

SUMMARY

This document provides methods and materials for treating a mammal (e.g., a human) having one or more tumors. For example, embolic agents including an amnion tissue preparation (e.g., embolic agents coated with an amnion tissue preparation, also referred to as "amnion coated embolic agents") provided herein can be used in arterial embolization to reduce and/or eliminate blood flow in a blood vessel that supplies a tumor. In some cases, amnion coated embolic agents provided herein can be used to treat a mammal having one or more tumors.

Tumors cannot survive and grow without the oxygen and nutrients supplied by the vasculature. As described herein, reducing and/or eliminating blood flow in a blood vessel that supplies a tumor can deprive the tumor of the oxygen-carrying blood and other substances it needs to grow, thereby starving the tumor cells.

In general, one aspect of this document features a composition comprising an embolic agent having a coating including an amnion tissue preparation. The embolic agent can be a microparticle. The embolic agent can be a microsphere. The embolic agent can include a bio-compatible material. The bio-compatible material can be gelatin (e.g., tris-acryl gelatin), polyvinyl alcohol, ethylene vinyl alcohol copolymer, poly(lactic-co-glycolic acid), N-butyl-2 cyanoacrylate, collagen, thrombin, glue, calcium alginate, latex, silicon, starch, cellulose, chitosan, butyl cyanoacrylate, ethiodol, ethanol, ethanolamine oleate, sotradecol, or combinations thereof. The embolic agent can be resorbable. The embolic agent can be from about 0.5 μm to about 1200 μm in size. The amnion tissue preparation can include viable cells. The amnion tissue preparation can lack viable cells. The amnion tissue preparation can be a dried amnion tissue preparation (e.g., a dried amnion tissue preparation having a water content that is less than about 8 percent). The dried amnion tissue preparation can have a particle size ranging from about 0.1 μm to about 25 μm. The amnion tissue preparation can be the sole active ingredient. The embolic agent can be further coated with one or more therapeutic agents. The one or more therapeutic agents can include one or more angiogenesis inhibitors. The one or more therapeutic agents can include one or more chemotherapeutic agents. The one or more therapeutic agents can include one or more angiogenesis inhibitors and one or more chemotherapeutic agents.

In another aspect, this document features an artificial embolus comprising one or more compositions comprising an embolic agent having a coating including an amnion tissue preparation.

In another aspect, this document features a method for performing arterial embolization. The method includes, or consists essentially of, administering one or more compositions into a blood vessel of a mammal, where the composition includes an embolic agent having a coating including an amnion tissue preparation, where the one or more embolic agents form an embolus in the blood vessel, and where blood flow in the blood vessel is reduced. The mammal can be a human. The composition does not induce an inflammatory response in the mammal.

In another aspect, this document features a method for treating a tumor in a mammal. The method includes, or consists essentially of, administering one or more compositions into a blood vessel of a mammal where the composition comprises an embolic agent having a coating including an amnion tissue preparation, where the one or more embolic agents form an embolus in the blood vessel, and where the size of the tumor is reduced. The tumor can be a benign tumor. The benign tumor can be a uterine fibroid. The benign tumor can be a benign prostatic hyperplasia. The tumor can be a cancerous tumor. The cancerous tumor can be a liver cancer tumor. The liver cancer can be a hepatocellular carcinoma, a cholangiocarcinoma, or a sarcoma. The cancerous tumor can be a kidney cancer tumor. The kidney cancer can be a renal cell carcinoma. The mammal can be a human. The composition does not induce an inflammatory response in the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides embolic agents including an amnion tissue preparation (e.g., amnion coated embolic agents), as well as methods and materials for making and using embolic agents including an amnion tissue preparation. For example, one or more amnion coated embolic agents (e.g., embolic agents coated with an amnion tissue preparation) provided herein can be used in arterial embolization to form one or more emboli (e.g., artificial emboli)

that reduce and/or eliminate blood flow in a blood vessel. In some cases, one or more amnion coated embolic agents provided herein can be used to treat a mammal (e.g., a human) having one or more tumors. For example, one or more amnion coated embolic agents provided herein can be administered to a mammal to reduce and/or eliminate blood flow in a blood vessel that supplies a tumor in a mammal. In some cases, an amnion coated embolic agent can be used to deliver an amnion tissue preparation to a blood vessel (e.g., to promote healing in the blood vessel). Also provided herein are artificial emboli formed from one or more (e.g., one, two, three, four, five, six, seven, eight, nine, ten, or more) amnion coated embolic agents provided herein.

Any appropriate embolic agent can include (e.g., be coated with) an amnion tissue preparation (e.g., human amnion tissue preparation) as described herein. An embolic agent can be in the form of a gel, a liquid, or a particle (e.g., a nanoparticle, a microparticle, or a macroparticle). In some cases, an embolic agent can be designed to change forms (e.g., to be delivered as a liquid and form a gel or a particle within a blood vessel). An embolic agent that is a particle can be any appropriate shape (e.g., a sphere or a disk). In some cases, an embolic agent can be permanent (e.g., non-resorbable). In some cases, an embolic agent can be temporary (e.g., resorbable or dissolvable). Examples of embolic agents include, without limitation, beads (e.g., microspheres), plugs, foams (e.g., gelfoams), coils, and sponges. An embolic agent can include any appropriate material (e.g., a bio-compatible material). Examples of materials that can be used for an embolic agent include, without limitation, gelatin (e.g., tris-acryl gelatin), polyvinyl alcohol, ethylene vinyl alcohol copolymer, poly(lactic-co-glycolic acid), N-butyl-2 cyanoacrylate, collagen, thrombin, glue, calcium alginate, latex, silicon, starch, cellulose (e.g., carboxymethyl cellulose), chitosan (e.g., carboxymethyl chitosan), butyl cyanoacrylate, ethiodol, ethanol, ethanolamine oleate, sotradecol, and combinations thereof. In some cases, an embolic agent including an amnion tissue preparation can be a resorbable (e.g., bioresorbable) amnion coated embolic agents. For example, a resorbable amnion coated embolic agent can be a degradable starch microsphere.

In some cases, embolic agents described elsewhere (see, e.g., Vaidya et al., *Semin. Intervent. Radiol.*, 25:204-215 (2008); EmboMedics; and EmboCept® S) can be obtained, and can be coated with an amnion preparation as described herein.

An embolic agent can be any appropriate size. For example, when an embolic agent is a particle, the particle can be from about 0.5 µm to about 2200 µm (e.g., from about 0.5 µm to about 2000 µm, from about 0.5 µm to about 1750 µm, from about 0.5 µm to about 1500 µm, from about 0.5 µm to about 1250 µm, from about 0.5 µm to about 1000 µm, from about 0.5 µm to about 750 µm, 0.5 µm to about 500 µm, 0.5 µm to about 250 µm, 0.5 µm to about 100 µm, 0.5 µm to about 50 µm, from about 1 µm to about 2200 µm, from about 10 µm to about 2200 µm, from about 25 µm to about 2200 µm, from about 50 µm to about 2200 µm, from about 75 µm to about 2200 µm, from about 100 µm to about 2200 µm, from about 250 µm to about 2200 µm, from about 500 µm to about 2200 µm, from about 750 µm to about 2200 µm, from about 1000 µm to about 2200 µm, from about 1500 µm to about 2200 µm, from about 2000 µm to about 2200 µm, from about 1 µm to about 2000 µm, from about 5 µm to about 1500 µm, from about 10 µm to about 1000 µm, from about 25 µm to about 750 µm, from about 50 µm to about 500 µm, from about 100 µm to about 400 µm, from about 200 µm to about 300 µm, from about 1 µm to about 25 µm, from about 25 µm to about 50 µm, from about 50 µm to about 75 µm, or from about 75 µm to about 100 µm) in size (e.g., in diameter or as measured across the longest dimension).

Amnion coated embolic agents provided herein can include (e.g., be coated with) any appropriate amnion tissue preparation (e.g., human amnion tissue preparation). In cases where an embolic agent is a particle, the particle can be coated with an amnion tissue preparation. For example, embolic agents including an amnion tissue preparation (e.g., amnion coated embolic agents) can be completely coated with an amnion tissue preparation. In some cases, embolic agents including an amnion tissue preparation (e.g., amnion coated embolic agents) can be partially coated with an amnion tissue preparation.

The term "amnion tissue preparation" as used herein refers to a preparation of amnion tissue or amnion material. In some cases, an amnion tissue preparation can be a liquid preparation (e.g., solution or suspension) that is prepared from a dried amnion tissue preparation. The term "dried amnion tissue preparation" as used herein refers to a preparation of amnion tissue or amnion material that is dried to have a water content that is less than about 8 percent (e.g., less than about 7 percent, less than about 6 percent, less than about 5 percent, less than about 4 percent, less than about 3 percent, less than about 2 percent, or less than about 1 percent). In some cases, a dried amnion tissue preparation can have a water content that is between about 0.1 percent and about 8 percent (e.g., between about 0.5 percent and about 8 percent, between about 1 percent and about 8 percent, between about 0.1 percent and about 5 percent, between about 0.1 percent and about 4 percent, between about 0.1 percent and about 3 percent, between about 0.5 percent and about 5 percent, or between about 1 percent and about 4 percent).

An amnion tissue preparation can be dried using any appropriate technique such as micronization, vacuum drying, spray drying, freeze drying, or combinations thereof. In some cases, an amnion tissue preparation can be dried as described elsewhere (e.g., U.S. Pat. No. 5,656,498). A dried amnion tissue preparation can have any appropriate particle size. For example, a dried amnion tissue preparation can have a particle size ranging from about 0.1 µm to about 25 µm (e.g., from about 0.5 µm to about 25 µm, from about 0.75 µm to about 25 µm, from about 1 µm to about 25 µm, from about 0.1 µm to about 15 µm, from about 0.1 µm to about 10 µm, from about 0.1 µm to about 7.5 µm, from about 0.1 µm to about 5 µm, from about 0.75 µm to about 7.5 µm, or from about 1 µm to about 5 µm).

An amnion tissue preparation or a dried amnion tissue preparation can contain viable cells, non-viable cells, or a combination thereof. For example, an amnion tissue preparation or a dried amnion tissue preparation can be a preparation of amnion tissue or amnion material having viable cells. In some cases, an amnion tissue preparation can be a solution or suspension of amnion tissue or amnion material having viable cells.

In some cases, an amnion tissue preparation or a dried amnion tissue preparation can be a preparation of amnion tissue or amnion material where all the cells were removed, killed, or lysed such that the amnion tissue preparation or the dried amnion tissue preparation lacks viable cells. In some cases, an amnion tissue preparation or a dried amnion tissue preparation can be a preparation of amnion tissue or amnion material that was exposed to one or more physical and/or chemical treatments that killed, fixed, or lysed the cells of the amnion tissue or amnion material such that the amnion tissue preparation or the dried amnion tissue preparation lacks viable cells. For example, temperature (e.g., rapid freezing or rapid freezing-thawing), force and pressure, and/or electrical disruption can be used to kill or lyse cells within amnion tissue or amnion material to produce an amnion tissue preparation or a dried amnion tissue preparation that lacks viable cells.

In some cases, amnion tissue or amnion material can be obtained and then treated in a manner designed to lyse all the cells within the amnion tissue or amnion material. In these cases, the resulting material (e.g., matrix material and cellular remnants from lysed cells) can be used as an amnion tissue preparation that lacks viable cells or dried to form a dried amnion tissue preparation that lacks viable cells.

In some cases, an amnion tissue preparation or a dried amnion tissue preparation can be prepared from human amnion tissue. For example, human amnion tissue can be harvested, processed to maintain cell viability with or without removing blood, and used as an amnion tissue preparation or dried to form a dried amnion tissue preparation.

In some cases, human amnion tissue can be processed to remove blood prior to being used as an amnion tissue preparation or prior to being dried to form a dried amnion tissue preparation. In some cases, human amnion tissue can be processed without removing cells or blood prior to forming an amnion tissue preparation or a dried amnion tissue preparation.

An example of an amnion tissue preparation includes, without limitation, a human amnion tissue preparation that includes viable cells. In some cases, an amnion tissue preparation can be obtained from MiMedX® or a tissue bank (e.g., a human tissue bank).

In some cases, an amnion tissue preparation also can include one or more immunosuppressant agents (e.g., corticosteroids such as glucocorticoids), one or more anti-inflammatory agents (e.g., non-steroidal anti-inflammatory drugs, dexamethasone or other type of glucocorticoid steroids), one or more growth factors (e.g., epithelial growth factor (EGF), fibroblast growth factor-2 (FGF2), or stem cell factor (SCF)), one or more antimicrobial agents (e.g., antibiotics such as kanamycin, neomycin, streptomycin, or gentamicin, or an antifungal agent).

In some cases, an embolic agent including an amnion tissue preparation (e.g., amnion coated embolic agents) provided herein can include an amnion tissue preparation (e.g., human amnion tissue preparation) as the sole active ingredient. For example, when an embolic agent is an amnion coated embolic agent, an amnion coated embolic agent can include an amnion tissue preparation as the sole active ingredient.

In some cases, an embolic agent including an amnion tissue preparation (e.g., amnion coated embolic agents) provided herein can include an amnion tissue preparation (e.g., human amnion tissue preparation) and one or more other therapeutic agents. For example, when an embolic agent is an amnion coated embolic agent, an amnion coated embolic agent can include an amnion tissue preparation and one or more other therapeutic agents. Examples of therapeutic agents include, without limitation, nonsteroidal anti-inflammatory drugs (NSAIDs), cabergoline, selective progesterone receptor modulators, radiopharmaceuticals, immunosuppressive drugs, angiogenesis inhibitors (e.g., bevacizumab, axitinib, cabozantinib, lenalidomide, regorafenib, vandetanib, ziv-aflibercept, itraconazole, carboxyamidotriazole, TNP-470, CM101, IFN-α, IL-12, platelet factor-4, suramin, SU5416, thrombospondin, VEGFR antagonists, angiostatic steroids+heparin, cartilage-derived angiogenesis inhibitory factor, matrix metalloproteinase inhibitors, angiostatin, endostatin, 2-methoxyestradiol, tecogalan, tetrathiomolybdate, thalidomide, thrombospondin, prolactin, αVβ3 inhibitors, linomide, ramucirumab, tasquinimod, ranibizumab, sorafenib, sunitinib, pazopanib, and everolimus), and/or chemotherapeutic agents (including, but not limited to, alkylating agents (e.g., cyclophosphamide, mechlorethamine, chlorambucil, melphalan, dacarbazine, nitrosoureas, temozolomide), anthracyclines (e.g., daunorubicin, doxorubicin, epirubicin, idarubicin, mitoxantrone, and valrubicin), cytoskeletal disruptors (e.g., paclitaxel, docetaxel, abraxane, and taxotere), histone deacetylase inhibitors (e.g., vorinostat and romidepsin), topoisomerase inhibitors (e.g., irinotecan, topotecan, etoposide, teniposide, and tafluposide), kinase inhibitors (e.g., sorafenib, regorafenib, bortezomib, erlotinib, gefitinib, imatinib, vemurafenib, and vismodegib), nucleotide analogs and precursor analogs (e.g., azacitidine, azathioprine, capecitabine, cytarabine, doxifluridine, fluorouracil, gemcitabine, hydroxyurea, mercaptopurine, methotrexate, and tioguanine), peptide antibiotics (e.g., bleomycin and actinomycin), platinum-based agents (e.g., carboplatin, cisplatin, and oxaliplatin), retinoids (e.g., tretinoin, alitretinoin, and bexarotene), and vinca alkaloids and derivatives (e.g., vinblastine, vincristine, vindesine, and vinorelbine)).

In cases where an embolic agent including an amnion tissue preparation is an amnion coated embolic agent, an amnion tissue preparation can be coated onto an embolic agent to produce an amnion coated embolic agent provided herein using any appropriate method. For example, in cases where an amnion tissue preparation is a liquid preparation (e.g., solution or suspension), an embolic agent can be dipped into or sprayed with the liquid preparation.

This document also provides methods for using embolic agents including an amnion tissue preparation (e.g., amnion coated embolic agents) provided herein. For example, one or more amnion coated embolic agents (e.g., an effective amount of amnion coated embolic agents) can be administered to a mammal for use in arterial embolization. In some cases, one or more amnion coated embolic agents (e.g., an effective amount of amnion coated embolic agents) can be used to reduce or eliminate blood flow (e.g., blood flow supplying a tumor or hemorrhaging) in a blood vessel of a mammal. For example, a mammal having one or more tumors can be treated by administering one or more amnion coated embolic agents (e.g., an effective amount of amnion coated embolic agents) to reduce or eliminate blood flow supplying a tumor. In some cases, one or more amnion coated embolic agents (e.g., an effective amount of amnion coated embolic agents) can be used to deliver an amnion tissue preparation to a blood vessel (e.g., to promote healing in the blood vessel). Effective amounts of amnion tissue preparations described herein can be determined by a physician, taking into account various factors such as overall health status, body weight, sex, diet, time and route of administration, other medications, and any other relevant clinical factors. As used herein, an "effective amount" or "therapeutically effective amount" of a composition provided herein is the amount that is sufficient to provide a beneficial effect to the mammal to which the composition or preparations are delivered. In some cases, the effective amount can be the amount effective to reduce and/or eliminate blood flow in a blood vessel of a mammal. For example, the effective amount can be the amount effective to reduce the size of and/or eliminate a tumor in a mammal; to reduce and/or eliminate the number of cells in a tumor; and/or to achieve an improvement or elimination of one or more symptoms of a tumor (e.g., pain, weight loss, loss of appetite, frequent urination, difficulty emptying the bladder, constipation, and jaundice, depending on the type and location of the tumor(s)).

In some cases, one or more embolic agents including an amnion tissue preparation (e.g., amnion coated embolic agents) provided herein can be administered to a mammal as the sole embolic agent used in an arterial embolization.

In some cases, one or more embolic agents including an amnion tissue preparation (e.g., amnion coated embolic agents) provided herein can be administered to a mammal together with one or more additional embolic agents (e.g., drug-eluting embolic agents) in an arterial embolization. For example, one or more amnion coated embolic agents can be administered together with one or more embolic agents containing a chemotherapeutic drug (e.g., in a chemoembolization procedure such as transarterial chemoembolization (TACE)). For example, one or more amnion coated embolic agents can be administered together with one or more embolic agents containing a radioactive material (e.g., in a radioembolization procedure such as selective internal radiation therapy (SIRT)).

In some cases, one or more embolic agents including an amnion tissue preparation (e.g., amnion coated embolic agents) provided herein can be administered to a mammal in an arterial embolization without inducing an inflammatory response (e.g., an inflammatory response in the blood vessel).

Any appropriate technique can be used to administer one or more embolic agents including an amnion tissue preparation (e.g., amnion coated embolic agents) provided herein to a mammal. For example, one or more amnion coated embolic agents provided herein can be administered to a blood vessel in a mammal. In some cases, a catheter can be inserted through a percutaneous puncture in the arm or groin, and one or more amnion coated embolic agents provided herein can be administered to a blood vessel in a mammal via the catheter. In some cases, methods of using amnion coated embolic agents provided herein can include using a guidewire to guide a catheter to a blood vessel. In some cases, optical imaging (e.g., X-ray, fluoroscopic guidance, and/or radiopaque contrast dye) can be used to guide a catheter to a blood vessel.

Embolic agents including an amnion tissue preparation (e.g., amnion coated embolic agents) provided herein can be administered to any appropriate blood vessel. A blood vessel can be an artery, a vein, or a capillary. In some cases, a blood vessel can be a blood vessel supplying a tumor. In some cases, a blood vessel can be a hemorrhagic blood vessel. A blood vessel can be in any appropriate location of the body (e.g., the legs, the neck, the heart, the kidneys, the aorta, the chest, and the abdomen). Examples of blood vessels without limitation, a peripheral artery, a peroneal artery, a plantar artery (e.g., a lateral, medial, or deep plantar artery), a coronary artery, a renal artery, a hepatic artery, and uterine artery. In some cases, one or more amnion coated embolic agents can be administered to a first blood vessel, travel through the vasculature, and form an embolus in a second blood vessel.

In some cases, the methods and materials provided herein can be used to treat a mammal (e.g., a human) having one or more tumors. For example, one or more embolic agents including an amnion tissue preparation (e.g., amnion coated embolic agents) described herein can be administered to a mammal to reduce and/or eliminate blood flow in a blood vessel supplying a tumor in a mammal. In some cases, the methods provided herein can include reducing blood flow in a blood vessel supplying a tumor in a mammal by about 20% to about 100% (e.g., about 25% to about 95%, about 30% to about 90%, about 50% to about 80%, about 60% to about 75%, about 20% to about 80%, about 20% to about 50%, about 25% to about 50%, about 30% to about 100%, about 40% to about 100%, about 50% to about 100%, or about 75% to about 100%). For example, one or more embolic agents including an amnion tissue preparation (e.g., amnion coated embolic agents) described herein can be administered to a mammal to reduce and/or eliminate a tumor (e.g., reduce and/or eliminate the size of a tumor and/or reduce and/or eliminate the number of tumor cells in a tumor) in a mammal. In some cases, the methods provided herein can include reducing the size of a tumor in a mammal by about 20% to about 100% (e.g., about 25% to about 95%, about 30% to about 90%, about 50% to about 80%, about 60% to about 75%, about 20% to about 80%, about 20% to about 50%, about 25% to about 50%, about 30% to about 100%, about 40% to about 100%, about 50% to about 100%, or about 75% to about 100%). In some cases, the methods provided herein can include eliminating (e.g., completely reducing or reducing by 100%) a tumor in a mammal.

In some cases, the methods and materials provided herein can be used to deliver an amnion tissue preparation to a blood vessel. For example, one or more embolic agents including an amnion tissue preparation (e.g., amnion coated embolic agents) described herein can be administered to a mammal (e.g., a human) to deliver an amnion tissue preparation to a blood vessel. In some cases, the methods provided herein can include delivering, to mammal (e.g., a human), an amnion tissue preparation made with from about 0.01 milligrams (mg) to about 10 grams (g) (e.g., from about 0.01 mg to about 10 g, from about 0.1 mg to about 10 g, from about 1 mg to about 10 g, from about 10 mg to about 10 g, from about 100 mg to about 10 g, from about 1 g to about 10 g, from about 0.01 mg to about 5 g, from about 0.01 mg to about 1 g, from about 0.01 mg to about 100 mg, from about 10 mg to about 5 g, from about 100 mg to about 1 g, or from about 1 g to about 5 g) of amnion tissue preparation to a blood vessel of the mammal being treated.

Any type of mammal can be treated as described herein. Examples of mammals that can be treated with one or more embolic agents including an amnion tissue preparation (e.g., amnion coated embolic agents) provided herein include, without limitation, humans, non-human primates (e.g., monkeys), dogs, cats, horses, cows, pigs, sheep, rabbits, mice, and rats. For example, humans having one or more tumors can be treated with one or more amnion coated embolic agents provided herein.

In some cases, the methods provided herein can include identifying a mammal as having one or more tumors. A mammal can be identified as having a one or more tumors using any appropriate technique. Examples of techniques that can be used to identify a mammal as having a disease and/or disorder associated with tumors, without limitation, imaging techniques, biopsy techniques, and blood tests.

Once identified as having one or more tumors, a mammal can be administered one or more embolic agents including an amnion tissue preparation (e.g., amnion coated embolic agents) provided herein. For example, one or more amnion coated embolic agents provided herein can be administered in an arterial embolization procedure.

When treating a mammal (e.g., a human) having one or more tumors, a tumor can be any kind of tumor. A tumor can be benign (not cancerous), pre-malignant (pre-cancerous), or malignant (cancerous).

In some cases, a mammal having one or more tumors can have a disease and/or disorder associated with having tumors. Examples of diseases and/or disorders associated with having tumors include, without limitation, kidney lesions, liver lesions, cancers (e.g., liver cancers such as hepatocellular carcinoma (HCC), cholangiocarcinoma (CCA), and sarcoma; kidney cancers such as renal cell carcinoma (RCC); neuroendocrine tumors; and ocular melanoma), uterine fibroids, benign prostatic hyperplasias, arteriovenous fistulas (AVFs), and arteriovenous malformations (AVMs). In some cases, one or more embolic agents including an amnion tissue preparation (e.g., amnion coated embolic agents) provided herein can be used to treat a mammal having a benign tumor. For example, a human having uterine fibroids can be treated using an amnion coated embolic agent provided herein in an arterial embolization procedure described herein. In some cases, one or more embolic agents including an amnion tissue preparation (e.g., amnion coated embolic agents) provided herein can be used to treat a mammal having a cancer. For example, a human having HCC can be treated using an amnion coated embolic agent provided herein in an arterial embolization procedure described herein.

In some cases, the methods and materials provided herein also can be used to treat a mammal (e.g., a human) having excess and/or uncontrolled blood flow (e.g., hemorrhaging) in a blood vessel. For example, one or more embolic agents including an amnion tissue preparation (e.g., amnion coated embolic agents) described herein can be administered to a mammal (e.g., a human) to reduce and/or eliminate blood flow in a blood vessel. In some cases, the methods provided herein can include identifying a mammal as having excess and/or uncontrolled blood flow (e.g., hemorrhaging) in a blood vessel. A mammal can be identified as having excess and/or uncontrolled blood flow in a blood vessel using any appropriate technique (e.g., angiography (e.g., digital subtraction angiography (DSA) and coronary angiography), ultrasound (e.g., Doppler ultrasound and intravascular ultrasound), and imaging techniques). A mammal having excess and/or uncontrolled blood flow in a blood vessel can have a disease and/or disorder associated with hemorrhaging (e.g., recurrent coughing up of blood, aneurysm (e.g., cerebral aneurysm), internal bleeding (e.g., gastrointestinal bleeding), nosebleeds, varicocele, post-partum bleeding, surgical hemorrhage, and traumatic hemorrhage (e.g., splenic rupture or pelvic fracture)).

Methods for using one or more embolic agents including an amnion tissue preparation (e.g., amnion coated embolic agents) provided herein can be used as a combination therapy with one or more additional agents/therapies used to treat one or more tumors. For example, a combination therapy used to treat a tumor can include administering to the mammal (e.g., a human) one or more amnion coated embolic agents provided herein and one or more chemotherapeutic agents (including, but not limited to, alkylating agents (e.g., cyclophosphamide, mechlorethamine, chlorambucil, melphalan, dacarbazine, nitrosoureas, temozolomide), anthracyclines (e.g., daunorubicin, doxorubicin, epirubicin, idarubicin, mitoxantrone, and valrubicin), cytoskeletal disruptors (e.g., paclitaxel, docetaxel, abraxane, and taxotere), histone deacetylase inhibitors (e.g., vorinostat and romidepsin), topoisomerase inhibitors (e.g., irinotecan, topotecan, etoposide, teniposide, and tafluposide), kinase inhibitors (e.g., sorafenib, regorafenib, bortezomib, erlotinib, gefitinib, imatinib, vemurafenib, and vismodegib), nucleotide analogs and precursor analogs (e.g., azacitidine, azathioprine, capecitabine, cytarabine, doxifluridine, fluorouracil, gemcitabine, hydroxyurea, mercaptopurine, methotrexate, and tioguanine), peptide antibiotics (e.g., bleomycin and actinomycin), platinum-based agents (e.g., carboplatin, cisplatin, and oxaliplatin), retinoids (e.g., tretinoin, alitretinoin, and bexarotene), vinca alkaloids and derivatives (e.g., vinblastine, vincristine, vindesine, and vinorelbine)). For example, a combination therapy used to treat a tumor can include administering to the mammal (e.g., a human) one or more amnion coated embolic agents provided herein and subjecting the mammal to one or more tumor therapies (e.g., surgery and radiation). In cases where embolic agents including an amnion tissue preparation (e.g., amnion coated embolic agents) described herein are used in combination with one or more agents/therapies for treating a tumor, the one or more agents/therapies for treating a tumor can be administered/performed at the same time or independently. For example, arterial embolization with one or more amnion coated embolic agents provided herein can be performed first, and the one or more agents/therapies for treating a tumor can be administered second, or vice versa.

In some cases, the methods provided herein also can include confirming the location of the one or more embolic agents including an amnion tissue preparation (e.g., amnion coated embolic agents) administered to a mammal (e.g., a human) and/or confirming whether or not the one or more embolic agents including an amnion tissue preparation (e.g., amnion coated embolic agents) administered to a mammal (e.g., a human) have formed an embolus (e.g., an artificial embolus). For example, imaging techniques (e.g., DSA) can be performed to confirm the location of the one or more amnion coated embolic agents administered to a mammal and/or to confirm that the one or more amnion coated embolic agents administered to a mammal have formed an artificial embolus.

The invention will be further described in the following examples, which do not limit the scope of the invention described in the claims.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An artificial microparticle for use in arterial embolization to treat a tumor in a mammal, the microparticle comprising:
   a core comprising a synthetic biocompatible material selected from gelatin, polyvinyl alcohol, ethylene vinyl alcohol copolymer, poly(lactic-co-glycolic acid), N-butyl-2 cyanoacrylate, glue, calcium alginate, latex, silicon, chitosan, butyl cyanoacrylate, ethiodol, ethanol, ethanolamine oleate, sotradecol, and mixtures thereof; and
   a coating, wherein the coating comprises a material different from the core, the coating comprising an amnion tissue preparation lacking viable cells and comprising cellular remnants from lysed cells of the amnion tissue preparation.

2. The microparticle of claim 1, wherein the amnion tissue preparation is a dried amnion tissue preparation.

3. The microparticle of claim 2, wherein the dried amnion tissue preparation is prepared via micronization, vacuum drying, spray drying, freeze drying, or a combination thereof.

4. The microparticle of claim 1, wherein the amnion tissue preparation has a water content of less than about 8 percent.

5. The microparticle of claim 1, wherein the microparticle is a microsphere.

6. The microparticle of claim 1, wherein the microparticle is from about 0.5 μm to about 2200 μm in size.

7. The microparticle of claim 1, wherein the amnion tissue preparation is from about 0.1 μm to about 25 μm in size.

8. The microparticle of claim 1, wherein the biocompatible material is resorbable.

9. The microparticle of claim 1, wherein the amnion tissue preparation lacking viable cells is amnion tissue with cells removed, killed, or lysed.

10. The microparticle of claim 1, wherein the amnion tissue preparation completely coats the microparticle.

11. The microparticle of claim 1, wherein the amnion tissue preparation partially coats the microparticle.

12. The microparticle of claim 1, further comprising one or more therapeutic agents.

13. The microparticle of claim 1, wherein the amnion tissue preparation further comprises at least one additional therapeutic agent selected from an immunosuppressant agent, an anti-inflammatory agent, a growth factor, an antimicrobial agent, and combinations thereof.

14. The microparticle of claim 1, wherein the amnion tissue preparation further comprises at least one additional therapeutic agent selected from a chemotherapeutic agent and an angiogenesis inhibitor.

15. The microparticle of claim 1, wherein the microparticle is selected from a bead, a plug, a foam, a coil, and a sponge.

* * * * *